US005766958A

United States Patent [19]
Sullivan et al.

[11] Patent Number: 5,766,958
[45] Date of Patent: Jun. 16, 1998

[54] METHOD FOR DETECTING AND COLLECTING INFECTIOUS AIRBORNE MICROORGANISMS FOR RAPID IDENTIFICATION

[76] Inventors: George D. Sullivan; Daniel J. Sullivan, both of 2317 Central St., Evanston, Ill. 60201; William J. Sullivan, 7241 N. Odell St., Chicago, Ill. 60631

[21] Appl. No.: 527,266

[22] Filed: Sep. 12, 1995

[51] Int. Cl.$^6$ .................................................. G01N 1/28
[52] U.S. Cl. .................. 436/174; 95/189; 95/202; 422/28; 422/32; 422/101; 435/30; 435/31; 435/308.1; 435/309.1; 436/176; 436/177
[58] Field of Search ........................ 436/174, 176, 436/177; 422/101, 28, 32; 435/30, 31, 308.1, 309.1; 55/223, 226–229, 237, 238, 244, 256, 257.4, 257.5, 279; 261/78.1, 78.2, 83; 95/159, 169, 170, 185, 186, 188, 189, 195, 198, 202, 219, 230, 237

[56] References Cited

U.S. PATENT DOCUMENTS

| | | | |
|---|---|---|---|
| 3,698,158 | 10/1972 | Kinnebrew | 55/227 |
| 3,824,770 | 7/1974 | Eckstein . | |
| 3,856,487 | 12/1974 | Perez . | |
| 3,881,993 | 5/1975 | Freake et al. | 435/30 |
| 4,172,865 | 10/1979 | Steier . | |
| 4,576,618 | 3/1986 | Wooldridge . | |
| 4,682,991 | 7/1987 | Grethe et al. | 55/223 |
| 5,009,869 | 4/1991 | Weinberg . | |
| 5,141,538 | 8/1992 | Derington . | |
| 5,185,371 | 2/1993 | Rubinstein | 422/28 |
| 5,225,158 | 7/1993 | Tayebi . | |
| 5,225,167 | 7/1993 | Wetzel . | |

OTHER PUBLICATIONS

Millie P. Schafer, Ph.D., "Sampling and Analytical Method Development for Airborne Mycobacterium Tuberculosis" (Aug. 30, 1994).

Walton Laboratories, "The Centrifugal Atomizer," May 1994 (Instruction Manual).

*Primary Examiner*—Jan Ludlow
*Attorney, Agent, or Firm*—Niro, Scavone, Haller & Niro

[57] ABSTRACT

A method and device for detecting airborne, infectious microorganisms in indoor air and collecting them for rapid identification. Diseased air is drawn into an enclosed chamber where it is percolated through a liquid such that many of the microorganisms become encapsulated in the liquid. The liquid is then atomized to ensure encapsulation of microorganisms which may have escaped encapsulation in the percolation step, and then separated from the air. The relatively slow drawing rate and delicate percolation through the liquid preserves the integrity of the microorganisms. The air is released into the room, while the microorganism-containing liquid is directed to a reservoir from which samples may be extracted for analysis. The liquid is recycled.

19 Claims, 3 Drawing Sheets

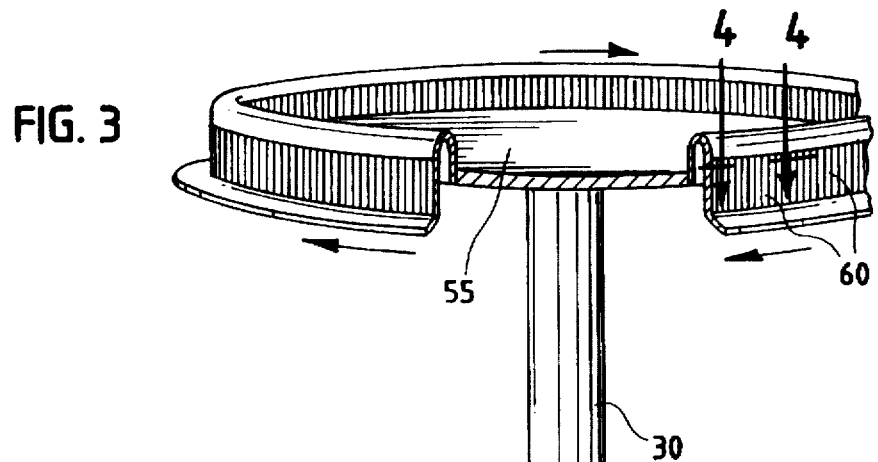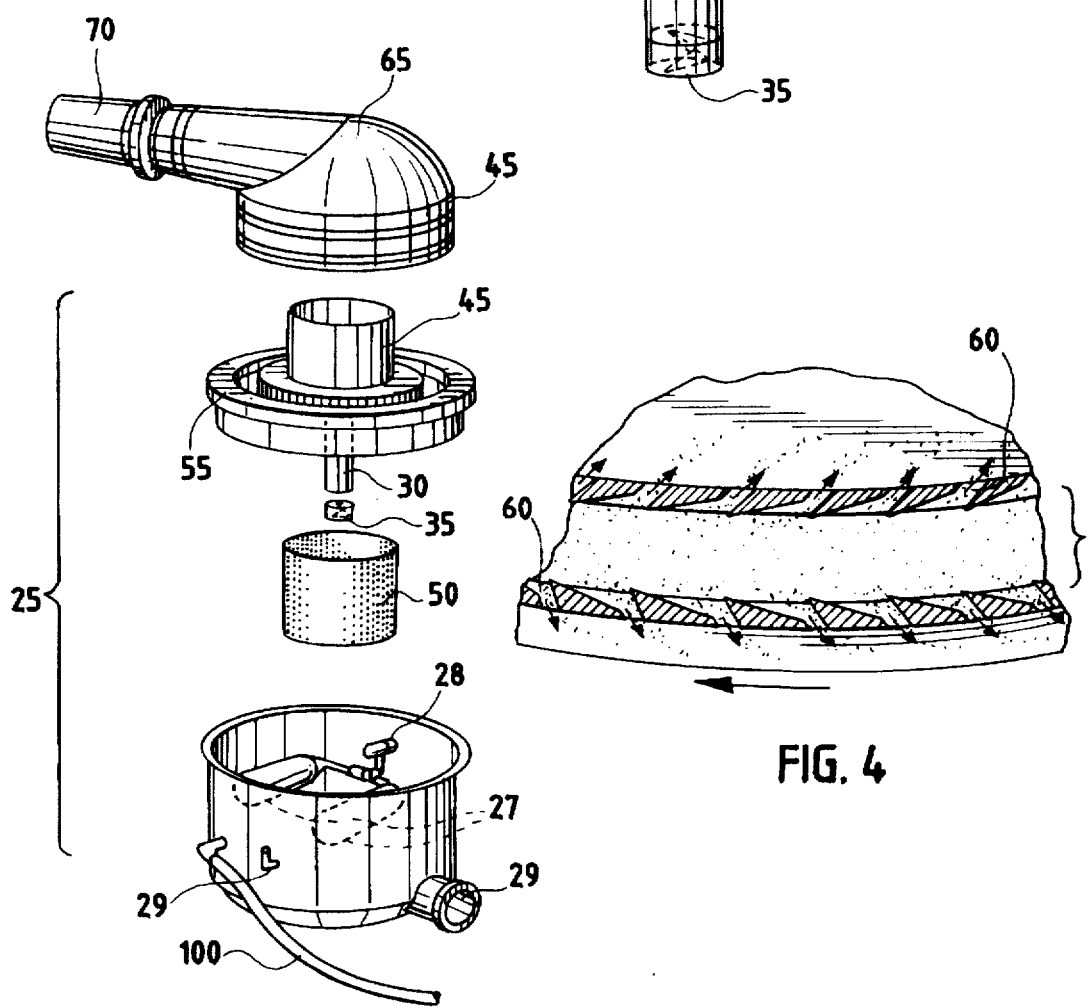

METHOD FOR DETECTING AND COLLECTING INFECTIOUS AIRBORNE MICROORGANISMS FOR RAPID IDENTIFICATION

TECHNICAL FIELD OF THE INVENTION

This invention relates to a new and useful process and apparatus for detecting airborne, infectious microorganisms in indoor air and collecting them for rapid identification.

BACKGROUND OF THE INVENTION

Due to recent outbreaks of highly infectious disease attributable to airborne microorganisms,in indoor air the need has arisen for apparatus and rapid methods for detecting and collecting infectious airborne microorganisms such as viruses, bacteria, molds, yeasts, and spores for rapid identification. Sneezing, coughing, and even speaking by an individual suffering from pulmonary tuberculosis, for example, can result in the release of large quantities of mycobacteria-containing particles into indoor air. The larger particles fall to the floor or other surfaces. These become dust-associated mycobacterial particles and are not believed to pose a serious health risk due to their larger size. The smaller mycobacterial-containing particles, however, undergo rapid evaporation and remain airborne indefinitely. Sub-micron size particles pose a serious risk of lower respiratory tract infection and disease. Tubercle bacilli are exceptionally hardy; the long-term viability of these microorganisms is unknown.

Thus a special need for detecting and collecting infectious airborne microorganisms for rapid identification exists, especially in places where disease can be readily spread from one person to another, such as in prisons, hospitals, homeless shelters, classrooms, and the workplace.

Presently, however, no method or apparatus exists to detect and collect airborne microorganisms in indoor air for rapid identification. The most commonly used protective device is the HEPA (High Efficiency Particulate Air) filter. This device is unsatisfactory because it becomes clogged with living, breeding microorganisms and offers little or no protection from microorganisms which are smaller than its smallest orifice. These pathogenic microorganisms can bypass the HEPA filter as well as nasal and throat defenses and reach the lungs. Also, the HEPA filter is useful only if the microorganisms are culturable. Many are not.

An alternative to the HEPA filter is a system which kills, but does not collect, pathogenic microorganisms by subjecting them to ultraviolet radiation. This system is not widely used, however, because it exposes workers and others to potentially harmful radiation. The room air sterilizer claimed in U.S. Pat. No. 5,225,167 (Wetzel) combines the HEPA filter with a germicidal ultraviolet lamp. The lamp is positioned so as to kill the microorganisms trapped in the HEPA filter without exposing workers and others to radiation. This system does not collect the microorganisms for subsequent identification and offers no protection from sub-micron size microorganisms which are small enough to pass through the smallest orifices of the HEPA filter. For example, many viruses are 300–400 Angstroms in size; much smaller than the orifices of a HEPA filter.

Other alternatives are the impactors and impingers. An impactor drives diseased air against a series of sampling plates having successively smaller holes. The largest microorganisms are collected at the first stage and smaller microorganisms are collected at later stages. While impactors collect microorganisms for identification, they, like the HEPA filter, suffer from the drawbacks of allowing submicron size microorganisms to escape and of dealing with living microorganisms.

The liquid impinger employs a compressor to draw diseased air at nearly sonic velocity into a liquid medium. This methodology, however, disintegrates many cells, which distorts and impedes the detection and collection of the pathogens, particularly those of less than one micron in size. Moreover, the necessity of a compressor renders a liquid impinger impractical for hospital use.

Consequently there remains a need for a method and apparatus for detecting the presence of airborne infectious microorganisms in indoor air and collecting these microorganisms for rapid identification which can be used in any indoor living or work space.

SUMMARY OF THE INVENTION

The present invention has reduced or eliminated the problems associated with the devices and processes heretofore known. It relates to a method for detecting and collecting airborne infectious microorganisms in indoor air by drawing the diseased air into an enclosed chamber where it comes into contact with a percolating liquid such that the microorganisms become encapsulated in the liquid; atomizing the microorganism-containing liquid to ensure encapsulation of microorganisms which may have escaped encapsulation in the percolation step; separating the microorganisms-containing liquid from the air; releasing the air back into the room; collecting the microorganism-containing liquid in a reservoir; extracting a sample from the microorganism-containing liquid; and recycling the liquid.

The liquid may be distilled water or a liquid disinfectant. The liquid disinfectant kills the microorganisms on contact; the distilled water preserves them for culturing. Because the microorganisms come into contact with liquid at numerous points during the process, a large number of microorganisms become encapsulated in the liquid. The combination of a relatively slow drawing rate and a delicate percolation through the liquid disinfectant preserves the integrity of the microorganisms. The microorganisms each sample may be identified using known analytical methods such as microscopy, the polymerase chain reaction (PCR) method, integrated electronic circuitry method, or any other DNA identification method.

BRIEF DESCRIPTION OF THE DRAWINGS

The invention will be better understood by reference to the drawings.

FIG. 2 is an exploded perspective view of the enclosed chamber portion of the apparatus for detecting the presence of airborne, infectious microorganisms in indoor air and collecting the microorganisms for rapid identification;

FIG. 3 is a perspective view of the generally vertically positioned pipe stem and generally horizontally positioned spinning circular plate with raised combed ridges at its periphery;

FIG. 4 is an enlarged, fragmentary view of the raised combed ridges portion of the generally horizontally positioned, variable speed, spinning circular plate;

DETAILED DESCRIPTION OF AN EMBODIMENT OF THE INVENTION

Figure 1:
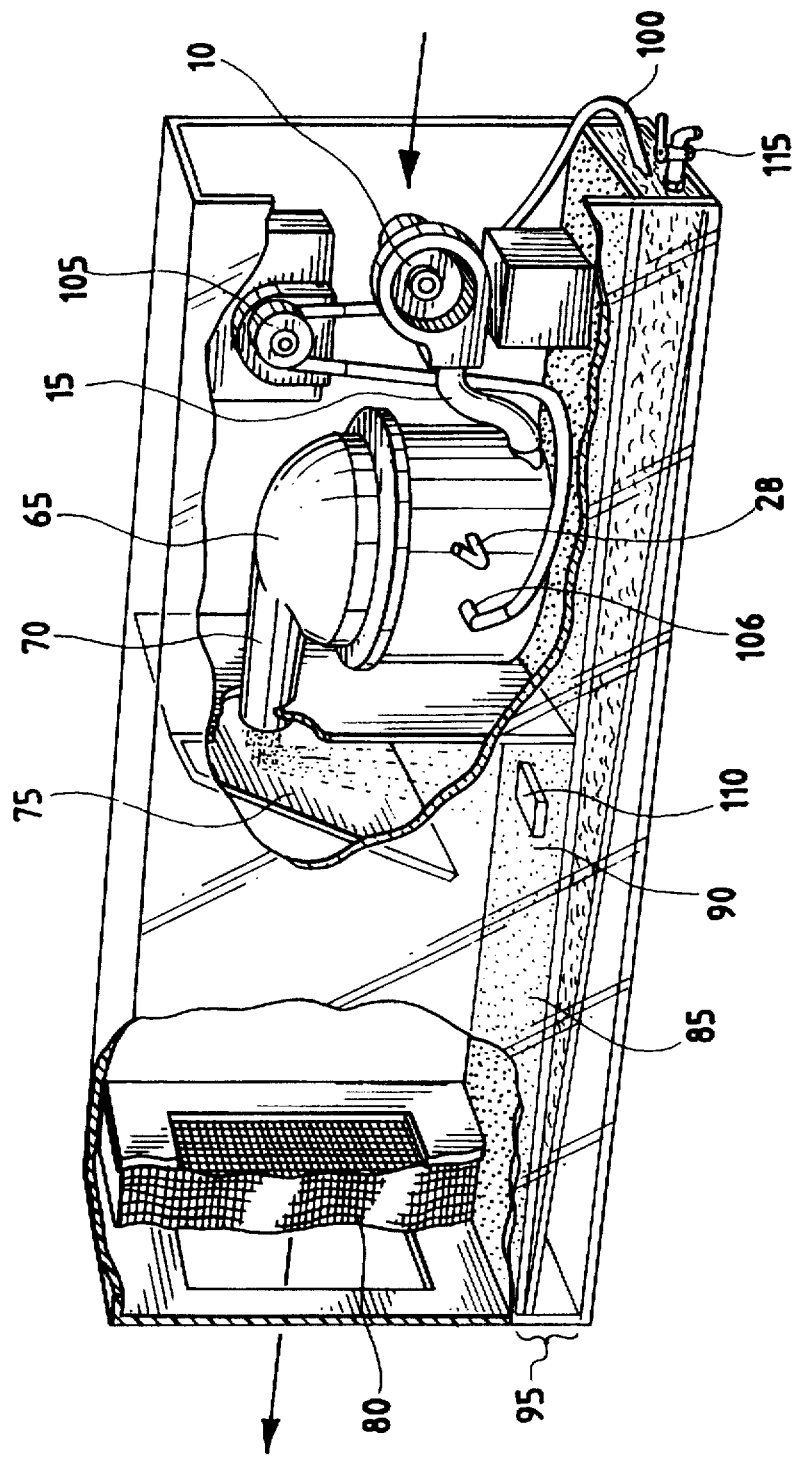
FIG. 1 is a perspective view of the apparatus for detecting the presence of airborne, infectious microorganisms in indoor air and collecting the microorganisms for rapid identification.

One embodiment of the invention employs a modified humidifier (Walton Manufacturing Co. Model WF-HP-226). The reservoir of the modified humidifier is filled with a liquid disinfectant of sufficient concentration to kill microorganisms on contact. Three and one-half liters of a mixture of 100 to 300 parts distilled water to 1 part Lysol® brand liquid disinfectant (active ingredients: o-phenylphenol, o-benzyl-o-cholophenol, soap, ethyl alcohol, xylenol, isopropyl alcohol, tetrasodium ethylenediamine tetraacetate) has been found to be effective with a wide variety of microorganisms. Alternatively, the reservoir may be filled with distilled water so that the microorganisms are not killed on contact but instead are preserved for culturing.

The diseased air is drawn directly into the liquid reservoir, at a level below the surface of the liquid, by a variable speed fan. A drawing rate of 15 to 150 cubic feet per minute is preferred because a drawing rate of greater than 150 cubic feet per minute may disintegrate and otherwise damage the microorganisms, thereby impeding and distorting the collection and analysis of the microorganisms. The diseased air is percolated through the liquid disinfectant reservoir. A generally vertically positioned stem pipe communicates at one end with the liquid in the reservoir and at the other end with a generally horizontally positioned, variable-speed, spinning circular plate. In the present embodiment, the stem pipe is 4⅛ inches in length and has a diameter of ⅝ inch. An impeller in the end of the stem pipe continuously impels portions of the liquid upward through the pipe stem to the surface of the spinning plate. In the present embodiment, this plate has a diameter of 6 inches. The speed with which the circular plate spins may be varied, but the speed must be sufficient to propel the liquid to the circumference of the plate. Speeds in the range of 3000 to 4000 revolutions per minute have been found to be suitable. The liquid is propelled, by centrifugal force, to the circumference of the plate and through raised combed ridges at the circumference of the plate. In the present embodiment, the combs are ⅝ inches in height and there is a space of 1/16 inch between each comb. This produces a plurality of vapor particles of approximately 25 microns in size. The vapor is spewed throughout the upper portion of the enclosed chamber, and a portion of the vapor is ejected from the chamber through a spout. The spout discharges to an angled strike plate which deflects the airstream downward to the floor of the housing. The strike plate serves to condense the pathogen-containing liquid. The rate of condensation can be increased if the strike plate is equipped with cooling coils or a thermo-electric module. The liquid drips into false-bottom chamber where it is pumped to a main reservoir from which samples may be extracted for analysis. The balance of the liquid is recycled into the reservoir for further use. This embodiment of the invention can be employed to evacuate substantially all the diseased air from a room.

The invention can also be employed simply to detect the presence of pathogenic microorganisms in indoor air. In this embodiment of the invention, a portion of the liquid may diverted from the false-bottom chamber to a test tube containing a fluorescent compound which fluoresces under ultraviolet light when exposed to particular species of microorganism. Becton Dickinson Company manufactures such a compound for the detection of mycobacteria—the BBL MGIT Mycobacteria Growth Indicator Tube. After the fluorescent hue of the compound is detected either manually or by an automatic audible alarm, the room may be sealed and the microorganisms killed and collected by use of the first-described process.

In still another embodiment of the invention, pathogens in human bodily fluids may be detected, killed, and collected by inserting samples of the bodily fluid into the suction fan.

One embodiment of an apparatus that can be used in the practice of the invention is shown in FIGS. 1–5. The variable speed suction fan 10 draws ambient air containing microorganisms into the flexible hose or tubing 15, which discharges the flow of air into a reservoir 20 located in an enclosed chamber 25.

The reservoir contains a liquid disinfectant or distilled water. The liquid level is monitored and controlled by adjustable floats 27. Excess liquid may be drained through an overflow valve 28.

Figure 5:
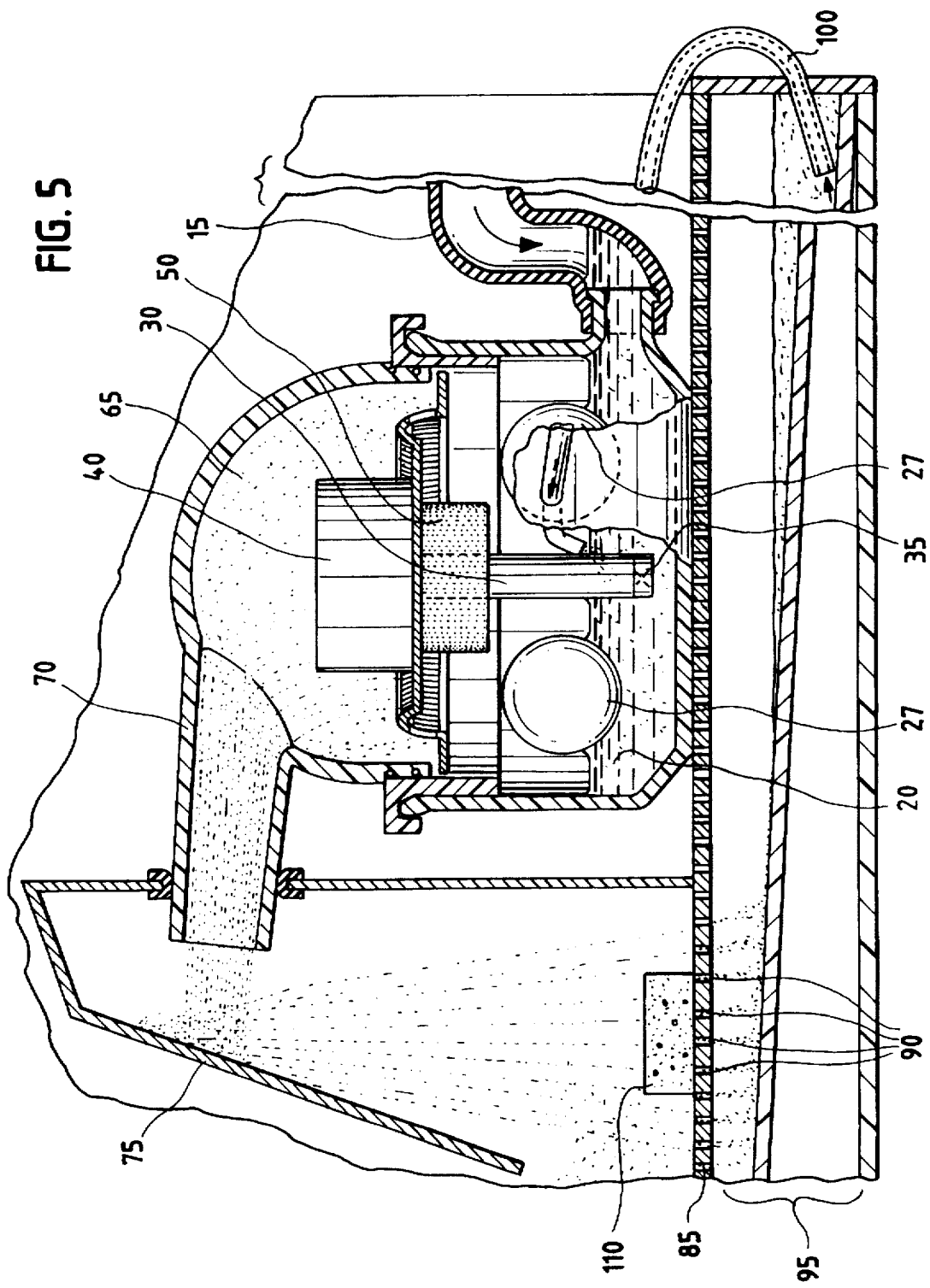
FIG. 5 is a side sectional view of the enclosed chamber, reservoir, false-bottom chamber, and strike plate portions of the apparatus for detecting the presence of airborne, infectious microorganisms in indoor air and collecting the microorganisms for rapid identification.

As shown in FIG. 5, the contaminated air is discharged into the reservoir 20 at a point 29 below the surface of the liquid so that it comes into immediate contact with and percolates through the liquid. The microorganisms in the contaminated air thereby become encapsulated in the liquid. Some of the liquid is vaporized by the percolating action in the reservoir and rise through the enclosed chamber 25. Most, however, remain within the reservoir 20 in liquid form.

The stem pipe 30 is equipped with an impeller 35, which is positioned below the surface of the liquid in the reservoir and is activated by the variable speed motor 40 in the upper housing 45 of the enclosed chamber 25. A cylindrical screen 50 surrounds the stem pipe 30 to prevent large particulates from entering the stem pipe.

The liquid, in which many of the pathogens have become encapsulated, is forced upward by the impeller 35 through the generally vertically positioned stem pipe 30 to a generally horizontally positioned spinning circular plate 55. As best shown in FIGS. 3 and 4, The liquid is discharged onto the spinning circular plate 55 and by centrifugal force is propelled through the raised combed ridges 60 along its circumference. The liquid is thereby atomized into a vapor, which is spewed into the domed top section 65 of the enclosed chamber 25. The upper and inner surface of the domed top section 65 becomes coated with a film of the disinfectant. If any microorganisms have thus far evaded collision with and encapsulation by the liquid, an opportunity for collision occurs on the upper and inner surface of the domed top 65. The relatively soft impingement throughout the area of the domed top results in the preservation of size and structure of sub-micron size microorganisms.

A substantial portion of the vapor exits through the venturishaped spout 70. The spout discharges to an angled strike plate 75. The strike plate 75 causes condensation of the vapor such that the liquid portion of the vapor remains on the strike plate and the gas portion travels toward the de-misting filter 80 from whence it is discharged into the room. The liquid portion of the vapor drips downward to the floor of the housing 85. On the floor of the housing 85, directly below the trailing edge of the angled strike plate is the series of the floor perforations 90 which allow the condensation or drippings of disinfectant to enter the inclined false-bottom chamber 95 and to gravitate along the inclined false-bottom chamber to a point where it wells up to the recycling feed tubing 100 and is drawn up by the recycling pump 105 and returned to the reservoir 20 by the recycling discharge tube 106 to complete the cycle and to begin a new cycle.

Finally, an absorbent membrane pad 110 is located directly above the floor perforations 90. This pad absorbs sufficient amounts of the captured or entrained microorganisms from which to extract a DNA sample for rapid PCR testing. Alternatively, the sample may be extracted from the reservoir 20 through a tap 115 which is attached to the false-bottom chamber 95.

While the invention has been described in detail with respect to a preferred embodiment, it should be understood that the invention is not limited to that embodiment. Rather, many modifications and variations would present themselves to those skilled in the art without departing from the concept, scope and spirit of this invention, as defined in the appended claims.

What is claimed is:

1. A method for collecting microorganisms from contaminated indoor air for rapid identification comprising the steps of:

drawing the contaminated indoor air into a liquid;
   percolating the contaminated air through the liquid;
   atomizing the liquid to create atomized liquid;
   separating the atomized liquid into gas and liquid components;
   collecting the liquid component of the atomized liquid; and
   extracting a sample from the liquid component of the atomized liquid containing the microorganisms;
   wherein the morphology of the microorganisms in the sample is preserved.

2. The method of claim 1 wherein the liquid is comprised of one part liquid disinfectant and 100 to 300 parts distilled water.

3. The method of claim 1 wherein the liquid is comprised of distilled water.

4. The method of claim 1 wherein the step of atomizing the liquid includes the step of forcing the liquid through an enclosed chamber from a reservoir to a spinning plate having raised combed ridges at its circumference such that the liquid is thrown through the combed ridges at the circumference of the spinning plate by centrifugal force.

5. The method of claim 1 wherein the step of separating the atomized liquid into gas and liquid components includes the step of forcing the atomized liquid against a strike plate such that a portion of the liquid component of the atomized liquid condenses on the strike plate and drips into a collection pool.

6. The method of claim 1 including releasing the gas component into the indoor air by passing the gas component through a de-misting filter.

7. The method of claim 1 wherein the step of extracting a sample includes the step of trapping a portion of the liquid portion of the atomized liquid in a membrane pad.

8. The method of claim 1 wherein the extracted sample is analyzed using a polymerase chain reaction analysis.

9. The method of claim 1 wherein the extracted sample is analyzed using an integrated electronic circuitry analysis.

10. The method of claim 1 wherein the microorganisms in the contaminated indoor air are detected by exposing the sample to a detecting compound.

11. The method of claim 1 wherein a portion of the liquid component of the atomized liquid that is not extracted as the sample is returned to a reservoir for reuse as the liquid.

12. A method for collecting microorganisms from contaminated indoor air for rapid identification comprising the steps of:

drawing the contaminated indoor air into an enclosed chamber;
    forcing the contaminated indoor air into liquid located in the enclosed chamber;
    percolating the contaminated air through the liquid such that microorganisms in the contaminated air become encapsulated in the liquid;
    atomizing the liquid in the enclosed chamber to create a vapor;
    condensing the vapor to create a liquid component and a gas component;
    collecting the liquid component in a collection pool;
    extracting a sample containing the microorganisms from the collection pool, wherein the morphology of the microorganisms in the sample is preserved; and
    pumping the liquid component from the collection pool to a reservoir.

13. The method of claim 12 wherein the liquid is comprised of one part liquid disinfectant and 100 to 300 parts distilled water.

14. The method of claim 12 wherein the liquid is comprised of distilled water.

15. The method of claim 12 wherein the step of condensing the vapor to create a liquid component and a gas component includes the step of forcing the vapor against a strike plate.

16. The method of claim 12 wherein the step of extracting a sample includes the step of trapping a portion of the liquid portion of the vapor in a membrane pad.

17. The method of claim 12 wherein the extracted sample is analyzed using a polymerase chain reaction analysis.

18. The method of claim 12 wherein the extracted sample is analyzed using an integrated electronic circuitry analysis.

19. The method of claim 12 wherein the microorganisms in contaminated indoor air are detected by exposing the sample to a detecting compound.

* * * * *